(12) United States Patent
Schubert et al.

(10) Patent No.: US 7,214,641 B2
(45) Date of Patent: May 8, 2007

(54) CATALYST AND HYDROGENATION OF CARBONYL COMPOUNDS IN THE LIQUID PHASE USING THE CATALYST

(75) Inventors: Markus Schubert, Ludwigshafen (DE); Michael Hesse, Worms (DE); Rolf-Hartmuth Fischer, Heidelberg (DE); Take Constantinescu, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 213 days.

(21) Appl. No.: 10/534,621

(22) PCT Filed: Nov. 6, 2003

(86) PCT No.: PCT/EP03/12379

§ 371 (c)(1),
(2), (4) Date: May 11, 2005

(87) PCT Pub. No.: WO2004/043592

PCT Pub. Date: May 27, 2004

(65) Prior Publication Data

US 2006/0052239 A1    Mar. 9, 2006

(30) Foreign Application Priority Data

Nov. 11, 2002   (DE) ................. 102 52 281

(51) Int. Cl.
*B01J 27/24* (2006.01)
*B01J 31/00* (2006.01)
*B01J 23/58* (2006.01)
*C08J 3/09* (2006.01)
*C07D 305/12* (2006.01)

(52) U.S. Cl. .............. 502/200; 502/102; 502/324; 502/330; 502/506; 502/512; 524/113; 549/313; 549/325; 549/326; 549/508

(58) Field of Classification Search ......... 502/200, 502/102, 324, 330, 506, 512; 524/113; 549/313, 549/325, 326, 508
See application file for complete search history.

(56) References Cited

U.S. PATENT DOCUMENTS

| | | | | |
|---|---|---|---|---|
| 3,840,475 A * | 10/1974 | Davis | .................. | 502/227 |
| 3,944,626 A * | 3/1976 | Honna et al. | ............... | 585/352 |
| 5,166,121 A * | 11/1992 | Khare et al. | ................ | 502/225 |
| 5,478,952 A * | 12/1995 | Schwartz | .................... | 549/325 |
| 6,225,477 B1 * | 5/2001 | Ernst et al. | ................. | 549/325 |
| 6,670,490 B1 * | 12/2003 | Campos et al. | ............ | 549/508 |
| 2003/0114719 A1 | 6/2003 | Fischer et al. | | |
| 2006/0004212 A1 * | 1/2006 | Bhattacharyya et al. | .... | 549/326 |

FOREIGN PATENT DOCUMENTS

| | | | |
|---|---|---|---|
| DE | 25 19 817 A1 | 11/1976 | |
| DE | 100 09 817 A1 | 9/2001 | |
| EP | 1 112 776 A1 | 7/2001 | |

OTHER PUBLICATIONS

"Thermal Structural Behavior and Properties of tetraamminecobalt (II) perrhenate. Electronic and Vibrational Spectra and Magnetic Properties of tetraamminecobalt (II) cation." Journal of Molecular Structure, vol. 15, Issue 2, Feb. 1973, pp. 289-299.*

* cited by examiner

*Primary Examiner*—Jerry A. Lorengo
*Assistant Examiner*—Patricia L. Hailey
(74) *Attorney, Agent, or Firm*—Connolly Bove Lodge & Hutz LLP

(57) ABSTRACT

The present invention provides a process for hydrogenating carbonyl compounds, in particular $C_4$-dicarboxylic acids to mixtures of tetrahydrofuran and gamma-butyrolactone, over supported rhenium catalysts, wherein rhenium and at least one further metal of groups VIII or Ib of the Periodic Table of the Elements, in particular ruthenium (Ru), rhodium (Rh), palladium (Pd), osmium (Os), iridium (Ir), platinum (Pt), copper (Cu), silver (Ag) or cobalt (Co), is applied to the support in the form of at least one bimetallic precursor compound, and also to these catalysts.

14 Claims, No Drawings

CATALYST AND HYDROGENATION OF CARBONYL COMPOUNDS IN THE LIQUID PHASE USING THE CATALYST

CROSS REFERENCE TO RELATED APPLICATION

The present application is a National Stage application of PCT/EP2003/012379, filed Nov. 6, 2003, which claims priority from German Patent Application No. DE 102 52 281.2, filed Nov. 11, 2002.

The invention relates to a process for hydrogenating compounds containing carbonyl groups in the liquid phase over supported rhenium catalysts which comprise at least one further active metal which is applied to the support together with the rhenium in the form of a bimetallic compound.

The industrial hydrogenation of compounds containing carbonyl groups, such as aldehydes, ketones, carboxylic acids, carboxylic anhydrides, with hydrogen over rhenium catalysts has been known for some time.

For instance DE-A 100 09 817 describes a supported rhenium catalyst which uses nonoxidatively pretreated activated carbon as the support material. The catalysts additionally contain further transition metals, in particular platinum group metals, in order to increase the activity. Rhenium and the further transition metals are applied to the support in the form of separate or combined solutions of their respective salts. The main product of the hydrogenations described is alcohols.

DE-A 2 519 817 discloses catalysts which at the same time comprise elements of group VII and VIII of the Periodic Table of the Elements. Preference is given to supported rhenium catalysts additionally comprising platinum or palladium. These catalysts comprise in particular rhenium and palladium which, preferably according to the examples, are applied simultaneously to the support in the course of catalyst preparation. According to the disclosure content of DE-A 2 519 817, it is also possible to apply the palladium compound first to the support. The activity of the supported palladium-rhenium catalysts in hydrogenations of compounds containing carbonyl groups to alcohols is so low that it becomes necessary to simultaneously use high pressures and high temperatures of from 215 to 230° C. As a consequence of the high energy and materials costs, carrying out the hydrogenations at high pressures and high temperatures is of low economic viability. In addition, the corrosivity, especially of the carboxylic acid solutions, increases under these conditions.

EP-A 1 112 776 discloses a process for hydrogenating $C_4$ dicarboxylic acids, their anhydrides or esters using a catalyst in which the rhenium component is distributed very uniformly on the support material. However, the palladium component present in addition exhibits a distinct coating profile, so that the synergistic effect which is presumably based on the formation of an intermetallic phase is only utilized to a limited extent. The catalysts described form gamma-butyrolactone with good selectivity. However, the product mixtures contain only traces of THF.

It is an object of the present invention to provide a catalyst for the hydrogenation of carbonyl compounds and also a process for hydrogenating carbonyl compounds, in particular dicarboxylic acids such as maleic acid and/or succinic acid or their anhydrides or esters, using this catalyst, said process allowing in particular mixtures having approximately equal proportions of optionally substituted gamma-butyrolactone ("GBL" hereinbelow) and tetrahydrofuran ("THF" hereinbelow) to be prepared and permits these mixtures to be prepared at good conversion with good overall selectivity.

We have found that this object is achieved by a supported rhenium catalyst for hydrogenating carbonyl compounds such as dicarboxylic acids and/or their derivatives, in particular maleic acid and/or succinic acid, their anhydrides and/or esters, in particular to mixtures of optionally substituted γ-butyrolactone and tetrahydrofuran, wherein rhenium and at least one further metal of groups VIII or Ib of the Periodic Table of the Elements, in particular ruthenium (Ru), rhodium (Rh), palladium (Pd), osmium (Os), iridium (Ir), platinum (Pt), copper (Cu), silver (Ag) or cobalt (Co), are applied to the support in the form of at least one bimetallic precursor compound.

In this context, a bimetallic precursor compound is a compound which comprises both a rhenium atom or cation and an atom or cation of the metal of groups VIII or Ib of the Periodic Table of the Elements.

The bimetallic precursor compound used is preferably a perrhenate double salt, more preferably one of the general formula I

$$[Me_a(NH_3)_b(OH)_c](ReO_4)_d \cdot eH_2O \qquad (I)$$

or a mixture thereof, where Me is a metal of groups VIII and Ib of the Periodic Table of the Elements, in particular Ru (ruthenium), Rh (rhodium), Pd (palladium), Os (osmium), Ir (iridium), Pt (platinum), Cu (copper), Ni (nickel), Ag (silver) or Co (cobalt), a is 1 or 2, b is an integer from 1 to 8, c is an integer from 0 to 5, d is 2, 3 or 4, and e is an integer from 0 to 12.

Double salts are mixed crystals of two salts. Anions and cations of an ionic crystal can be replaced by other cations and anions without the crystal structure type changing. When the mutually representative ion pair is arranged in the ion lattice not purely randomly, but rather by a certain distribution plan, this results in a double salt. The preparation of such double salts is known per se and described, for example, by Pechenyuk, S. I., Kuznetsov, V. Y., Popova, R. A., Zalkind, O. A., Zh. Neorg. Khim. 24 (1979) 3306.

The invention includes the recognition that the use of these double salts for applying the catalytically active components to the support achieves a uniform distribution of all catalytically active metals.

The bimetallic precursor compound used is more preferably $Pd(NH_3)_4(ReO_4)_2$ and/or $Pt(NH_3)_4(ReO_4)_2$.

Useful support materials are all support materials known for the preparation of hydrogen catalysts. Preference is given to silicon dioxide, aluminum oxide, titanium dioxide, zirconium dioxide, magnesium oxide, optionally pretreated activated carbon, graphitic carbon supports, nitrides, silicide, carbides or borides. The pretreatment mentioned may be an oxidative pretreatment, as described, for example, in EP-A 848 991. Preference is given to using supports of optionally pretreated activated carbon.

Rhenium (Re, calculated as the metal) and the further metal of group VIII or Ib of the Periodic Table are applied in an amount each of from 0.03 to 30% by weight, preferably from 1 to 12% by weight, more preferably from 2 to 5% by weight, based on the overall catalyst composed of support and active composition.

Further elements may be present on the catalyst. Examples include Zn (zinc), Sn (tin), Au (gold), Fe (iron), Mn (manganese), Cr (chromium), Mo (molybdenum), W (tungsten) and V (vanadium). Elements of groups VII, VIII or Ib of the Periodic Table of the Elements as rhenium (Re), platinum (Pt), ruthenium (Ru), silver (Ag) and palladium (Pd) may likewise additionally be present. These elements modify the catalyst substantially with regard to activity and selectivity (hydrogenolysis products) but are not essential. Their weight ratio to rhenium may be from 0 to 100, preferably from 0.5 to 30, more preferably from 0.1 to 5. The catalysts according to the invention are in particular preferably chromium-free.

The application of the active components rhenium and the further metal of group VIII or Ib of the Periodic Table of the Elements to the support can be carried out by impregnation in one or more steps with a solution of the particular dissolved bimetallic precursor compound in water, alcohol or prepared with another organic solvent, more preferably of the double salt of the general formula I, equilibrium adsorption in one or more steps of the bimetallic precursor compound dissolved in aqueous or alcoholic solution, more preferably of the double salt of the general formula I. In these processes, the active components are applied to the support material simultaneously and uniformly. Between the individual impregnation and equilibrium adsorption steps, there is in each case a drying step for removing the solvent. Preference is given to applying the active components by impregnation with an aqueous salt solution in one step.

To remove the solvents after the impregnation or equilibrium adsorption step, the impregnated catalyst is dried. The drying temperature is 30–350° C., preferably 40–280° C., more preferably 50–150° C.

The active components are distributed particularly evenly on the support of the catalyst according to the invention, and the intensity ratio of rhenium to metal (Me) of group VIII or Ib of the Periodic Table of the Elements over the entire catalyst particle in particular has deviations of less than a factor of 10 at more than 99.9% of the analyzed points, based on the statistical average, preferably deviations of less than a factor of 5 at 98% of the analyzed points on the catalyst surface and more preferably deviations of less than a factor of 2 in 80% of the analyzed points.

This factor was determined by SEM-EDX (Scanning electron microscope-energy dispersive x-ray spectroscopy). The method is known per se and described, for example, in Ulmanns Encyclopedia of Industrial Chemistry 6$^{th}$ Edition 2000 Electronic Release.

The catalysts are customarily activated before use. This activation may be effected by applying a reducing gas atmosphere to the catalyst. Preference is given to using an activation with the aid of hydrogen. The activation temperature is typically 100–500° C., preferably 130–400° C., more preferably 150–400° C. Alternative reduction methods are the reduction of the metallic components by contacting with a liquid reducing agent such as hydrazine, formaldehyde or sodium formate. The liquid reducing agent is typically contacted at temperatures of between 10 and 100° C. Preference is given to contacting at temperatures between 20 and 80° C.

The hydrogenation is carried out typically at 110–250° C., preferably at 150–250° C. Hydrogenation is effected typically at a reaction pressure between 5 and 220 bar, preferably 40 and 150 bar. The hydrogenation is carried out in the liquid phase, preferably in a fixed bed.

Suitable starting materials for the hydrogenation are generally carbonyl compounds which may additionally contain C—C double or triple bonds. Examples of aldehydes are propionaldehyde, butyraldehydes, crotonaldehydes, ethylhexanal, nonanal and glucose. Examples of carboxylic acids are succinic acid, fumaric acid, maleic acid. Esters include esters of the abovementioned acids, for example as the methyl, ethyl, propyl or butyl ester, and lactones, e.g. gamma-butyrolactone, delta-valerolactone or caprolactone, can also be used. It is also possible to use anhydrides such as succinic anhydride or maleic anhydride. Preferred starting materials are $C_4$ dicarboxylic acids and/or derivatives thereof, more preferably succinic acid, maleic acid, succinic anhydride, maleic anhydride and the esters of these acids. It will be appreciated that it is also possible to use mixtures of aldehydes, carboxylic acids, esters, anhydrides and/or lactones, preferably mixtures of carboxylic acids.

The compounds to be hydrogenated can be hydrogenated without solvent or in solution. Possible solvents include, for example, one of the hydrogenation products or materials are used such as alcohols such as methanol, ethanol, propanol or butanol, and also suitable are ethers such as THF or ethylene glycol ether or gamma-butyrolactone. A preferred solvent is water, especially in the hydrogenation of carboxylic acids.

The hydrogenation can be performed in the liquid phase, in one or more stages. In the liquid phase, both the suspension and the fixed bed method are possible. In the case of exothermic reactions, the heat can be removed by external coolant (for example tubular reactor). Evaporative cooling in the reactor is also possible, in particular when hydrogenation is effected without product recycling. In the case of product recycling, one possibility is a cooler in the recycle stream.

The process according to the invention is illustrated by the examples which follow.

EXAMPLES

Determination of the Intensity Factor using SEM-EDX

A Philips ESEM-XL30-FG SEM-EDX spectrometer with an EDX probe was used to measure the intensities (corresponding to the contents) of rhenium and of palladium. The analysis voltage was 30 kV. For preparation, the particles were divided in such a way that a clean cut surface was obtained. More than 300 μm of the cut surface were investigated for their content of Pd and Re by SEM-EDX in steps each of 15 μm. At each measurement point, a ratio of the intensities of Pd and Re can be calculated.

Example 1

15.83 g of $Pd(NO_3)_2$ were admixed with 8 g of 25% $NH_3$ solution and mixed with a solution of 8.66 g of $NH_4ReO_4$ in 98 g of water. The compound $Pd(NO_3)_2$ $(ReO_4)_2$ crystallized out. The product obtained by filtration was washed with water and dried.

Example 2

Catalyst A 1.11 g of the Pd—Re salt prepared according to Example 1 were dissolved at 80° C. in 20 g of water. 30 g of an activated carbon support (Degussa 180 from Degussa AG, Düsseldorf) were saturated with the solution of the Pd—Re salt at 70° C. The catalyst was then dried at 120° C. in 100 l (STP)/h of nitrogen ($N_2$). Subsequently, the catalyst was reduced with $N_2$ containing 0.5% of hydrogen ($H_2$) (100 l (STP)/h) at the same temperature for 30 min and at 200° C. for 30 min. The amount of hydrogen was then increased to 5% for 1 h and to 100% for a further two hours. Afterwards, the temperature was increased to 400° C. and the flow to 3000 l of $H_2$/h. The heating rates were in each case 5°

C./min. Finally, after cooling in $N_2$ at room temperature for 7 h, the catalyst was passivated in 5% of air in $N_2$. The catalyst contained 0.5% by weight of Pd and 2% by weight of Re.

Example 3

1.11 g of the Pd—Re salt were dissolved at 40° C. in 130 g of water. 10 g of this solution were applied with stirring to 30 g of the activated carbon support (Degussa 180). The catalyst was then dried at 120° C. for 1 h. After a washing step with water, the saturation and drying procedure was repeated until the entire solution had been applied to the support. Subsequently, the catalyst was dried and reduced in a similar manner to Example 2. The catalyst contained 0.5% by weight of Pd and 2% by weight of Re.

Example 4

A tubular reactor was charged with 20 g of catalyst A and purged with $N_2$ (240 l (STP)/h) at atmospheric pressure and 150° C. for 2 h. Subsequently, 5% of $H_2$ was mixed in, and the temperature was increased to 200° C. after two hours and maintained overnight. After switching to a 50% $H_2$—$N_2$ mixture, the temperature was increased to 230° C. for 1 h, and finally reduction was effected in 120 l (STP)/h of pure $H_2$ for a further 1 hour. Finally, the pressure was increased to 40 bar. This activated catalyst A was used to hydrogenate succinic anhydride (SAN) which was fed in an amount of 6.06 g/h as a 20% by weight solution in gamma-butyrolactone, at 235° C. and 40 bar in continuous operation. The molar $H_2$:SAN ratio was 35. At a conversion of 91%, a product yield of 81% (39% of tetrahydrofuran (THF) and 35% of γ-butyrolactone) was achieved.

Comparative Example 1

Catalyst C1

60 g of a water-premoistened activated carbon support (Degussa 180) were saturated with stirring with a solution containing 0.78 g of Pd $(NO_3)_2 2H_2O$ and 1.52 g of $HReO_4$ (72.8% by weight solution) in 20 ml of water at room temperature. Subsequently, the catalyst was treated in a similar manner to the drying and reduction described for Catalyst A in Example 2. The catalyst contained 0.5% by weight of palladium and 2% by weight of rhenium.

Comparative Example 2

20 g of catalyst C1 were installed in a tubular reactor and activated in a similar manner to Example 5. This activated catalyst A was used to hydrogenate succinic anhydride (SAN) which was metered in in an amount of 5.94 g/h as a 20% by weight solution in gamma-butyrolactone, at 235° C. and 40 bar in continuous operation. The molar $H_2$:SAN ratio was 35. At a conversion of 80%, a product yield of 77% (9% of tetrahydrofuran (THF) and 53% of γ-butyrolactone) was achieved.

We claim:

1. A supported rhenium catalyst, comprising rhenium and at least one further metal of groups VIII or Ib of the Periodic Table of the Elements, in the form of at least one perrhenate double salt of the general formula (I):

$$[Me_a(NH_3)_b(OH)_c](ReO_4)_d \cdot eH_2O \qquad (I)$$

wherein: Me is a metal of groups VIII and Ib of the Periodic Table of the Elements; a is 1 or 2; b is an integer from 1 to 8; c is an integer from 0 to 5; d is 2, 3 or 4; and e is an integer from 0 to 12; which is applied to the support as a bimetallic precursor compound.

2. The supported rhenium catalyst according to claim 1, wherein the bimetallic precursor compound is at least one compound selected from Pd $(NH_3)_4(ReO_4)_2$ and/or Pt $(NH_3)_4(ReO_4)_2$.

3. The supported rhenium catalyst according to claim 2, wherein rhenium and the further metal of group VIII or Ib of the Periodic Table of the Elements are present in an amount each of from 0.03 to 30% by weight, based on the entire catalyst.

4. The supported rhenium catalyst according to claim 2, wherein the ratio determined by electron microscopy of rhenium to metal (Me) of group VIII or Ib of the Periodic Table of the Elements over the entire catalyst particle shows deviations by a factor of less than 5 in 98% of the analyzed points.

5. The supported rhenium catalyst according to claim 1, wherein rhenium and the further metal of group VIII or Ib of the Periodic Table of the Elements are present in an amount each of from 0.03 to 30% by weight, based on the entire catalyst.

6. The supported rhenium catalyst according to claim 5, wherein the ratio determined by electron microscopy of rhenium to metal (Me) of group VIII or Ib of the Periodic Table of the Elements over the entire catalyst particle shows deviations by a factor of less than 5 in 98% of the analyzed points.

7. The supported rhenium catalyst according to claim 1, wherein the ratio determined by electron microscopy of rhenium to metal (Me) of group VIII or Ib of the Periodic Table of the Elements over the entire catalyst particle shows deviations by a factor of less than 5 in 98% of the analyzed points.

8. The process for preparing mixtures of tetrahydrofuran and gamma-butyrolactone by catalytic hydrogenation of carbonyl compounds, in the presence of a catalyst as claimed in claim 1.

9. The process according to claim 8, wherein the carbonyl compound is at least one compound selected from the group consisting of aldehydes, carboxylic acids, esters, and lactones.

10. The process according to claim 9, wherein the carbonyl compound is selected from the group consisting of maleic acid, fumaric acid, succinic acids, esters thereof, and anhydrides thereof.

11. The process according to claim 10, wherein the hydrogenation is carried out in the liquid phase over fixed bed catalysts at a pressure in the range from 5 to 220 bar and a temperature in the range from 110 to 250° C.

12. The process according to claim 9, wherein the hydrogenation is carried out in the liquid phase over fixed bed catalysts at a pressure in the range from 5 to 220 bar and a temperature in the range from 110 to 250° C.

13. The process according to claim 8, wherein the hydrogenation is carried out in the liquid phase over fixed bed catalysts at a pressure in the range from 5 to 220 bar and a temperature in the range from 110 to 250° C.

14. The supported rhenium catalyst according to claim 1, wherein Me is a metal selected from the group consisting of Ru, Rh, Pd, Os, Ir, Pt, Cu, Ni, Ag and Co.

* * * * *